(12) United States Patent
Houck

(10) Patent No.: US 8,551,952 B2
(45) Date of Patent: *Oct. 8, 2013

(54) METHODS FOR THE TREATMENT AND PREVENTION OF OCULAR DISORDERS

(75) Inventor: David Renwick Houck, Cary, NC (US)

(73) Assignee: Scynexis, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/458,460

(22) Filed: Apr. 27, 2012

(65) Prior Publication Data

US 2012/0270804 A1    Oct. 25, 2012

Related U.S. Application Data

(63) Continuation of application No. 12/301,210, filed as application No. PCT/US2007/011919 on May 18, 2007, now Pat. No. 8,188,052.

(60) Provisional application No. 60/802,208, filed on May 19, 2006.

(51) Int. Cl.
    A61K 38/13    (2006.01)
    A61P 27/02    (2006.01)

(52) U.S. Cl.
    USPC ........................................ 514/20.5; 514/20.8

(58) Field of Classification Search
    None
    See application file for complete search history.

(56) References Cited

U.S. PATENT DOCUMENTS

| | | | |
|---|---|---|---|
| 4,649,047 A | 3/1987 | Kaswan |
| 4,703,033 A | 10/1987 | Seebach |
| 4,771,122 A | 9/1988 | Seebach |
| 4,798,823 A | 1/1989 | Witzel |
| 4,814,323 A | 3/1989 | Andrieu et al. |
| 4,885,276 A | 12/1989 | Witzel |
| 4,996,193 A | 2/1991 | Hewitt et al. |
| 5,294,604 A | 3/1994 | Nussenblatt |
| 5,846,964 A | 12/1998 | Ozeki |
| 5,863,550 A | 1/1999 | Maeda et al. |
| 5,948,755 A | 9/1999 | Barriere et al. |
| 5,948,884 A | 9/1999 | Luchinger |
| 5,965,527 A | 10/1999 | Barriere et al. |
| 5,977,067 A | 11/1999 | Evers et al. |
| 5,981,479 A | 11/1999 | Ko et al. |
| 5,994,299 A | 11/1999 | Barriere et al. |
| 6,254,860 B1 | 7/2001 | Garst |
| 6,350,442 B2 | 2/2002 | Garst |
| 6,444,643 B1 | 9/2002 | Steiner et al. |
| 6,521,595 B1 | 2/2003 | Kim et al. |
| 6,583,265 B1 | 6/2003 | Ellmerer-Muller et al. |
| 6,927,208 B1 | 8/2005 | Wenger et al. |
| 7,196,161 B2 | 3/2007 | Fliri et al. |
| 7,226,905 B2 | 6/2007 | Viskov |
| 7,576,057 B2 | 8/2009 | Scribner et al. |
| 7,718,767 B2 | 5/2010 | Fliri et al. |
| 7,754,685 B2 | 7/2010 | Houck |
| 2003/0022831 A1* | 1/2003 | Rothbard et al. ............... 514/12 |
| 2004/0087496 A1 | 5/2004 | Kim et al. |
| 2004/0254117 A9 | 12/2004 | Saksena et al. |
| 2005/0277584 A1 | 12/2005 | Tien et al. |
| 2006/0089301 A1 | 4/2006 | Fliri et al. |
| 2006/0160727 A1 | 7/2006 | Fliri et al. |
| 2007/0173440 A1 | 7/2007 | Houck |
| 2007/0275884 A1 | 11/2007 | Hijikata et al. |
| 2008/0171699 A1 | 7/2008 | Scribner et al. |
| 2008/0255038 A1 | 10/2008 | Hopkins et al. |
| 2009/0298751 A1 | 12/2009 | Houck et al. |
| 2009/0306033 A1 | 12/2009 | Li et al. |
| 2009/0312300 A1 | 12/2009 | Li et al. |
| 2010/0167996 A1 | 7/2010 | Fliri et al. |
| 2010/0173836 A1 | 7/2010 | Li et al. |
| 2010/0173837 A1 | 7/2010 | Hopkins |
| 2010/0227801 A1 | 9/2010 | Hopkins |
| 2011/0144005 A1 | 6/2011 | Li et al. |

FOREIGN PATENT DOCUMENTS

| | | |
|---|---|---|
| EP | 2 023 918 B1 | 3/2011 |
| FR | 2 757 521 A1 | 6/1998 |
| WO | WO 98/28328 | 7/1998 |
| WO | WO 98/28329 | 7/1998 |
| WO | WO 98/28330 | 7/1998 |

(Continued)

OTHER PUBLICATIONS

STIC search notes dated Dec. 13, 2012, 2 pages.*
ISA/US PCT International Search Report dated Feb. 26, 2009, for International Application No. PCT/US2007/011919, filed May 18, 2007.
ISA/US PCT International Written Opinion dated Feb. 26, 2009, for International Application No. PCT/US2007/011919, filed May 18, 2007.
ISA/US PCT International Preliminary Report on Patentability dated Mar. 3, 2009, for International Application No. PCT/US2007/011919, filed May 18, 2007.
EPO Supplemental European Search Report, dated Jul. 18, 2008, for European Application No. EP 05815625.8, filed Sep. 30, 2005.

(Continued)

*Primary Examiner* — Satyanarayana R Gudibande
(74) *Attorney, Agent, or Firm* — Jones Day

(57) ABSTRACT

Provided herein are methods for treatment of ocular diseases. The methods comprise administering a compound of general Formula (I): wherein $R^1$, $R^2$, $R^3$, $R^4$ and Ak are as defined in the specification.

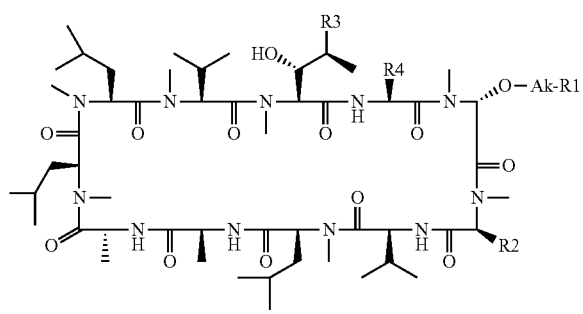

(I)

7 Claims, No Drawings

(56) References Cited

FOREIGN PATENT DOCUMENTS

| | | |
|---|---|---|
| WO | WO 99/32512 | 7/1999 |
| WO | WO-99/65933 | * 12/1999 |
| WO | WO 99/65933 | 12/1999 |
| WO | WO 99/67280 | 12/1999 |
| WO | WO 00/01715 | 1/2000 |
| WO | WO 00/61168 | 10/2000 |
| WO | WO 01/47883 | 5/2001 |
| WO | WO 2004/041221 | 5/2004 |
| WO | WO 2005/000308 | 1/2005 |
| WO | WO 2005/021028 | 3/2005 |
| WO | WO 2006/005580 | 1/2006 |
| WO | WO 2006/005610 | 1/2006 |
| WO | WO 2006/038088 | 4/2006 |
| WO | WO 2006/039163 | 4/2006 |
| WO | WO 2006/039668 | 4/2006 |
| WO | WO 2006/071618 | 7/2006 |
| WO | WO 2006/071619 | 7/2006 |
| WO | WO 2007/041631 | 4/2007 |
| WO | WO 2007/041632 | 4/2007 |
| WO | WO 2007/136759 | 11/2007 |
| WO | WO 2008/069917 | 6/2008 |
| WO | WO 2008/127613 | 10/2008 |
| WO | WO 2008/143996 | 11/2008 |
| WO | WO 2009/148615 | 12/2009 |
| WO | WO 2010/002428 | 1/2010 |
| ZA | 98/11531 | 12/1998 |

OTHER PUBLICATIONS

EPO European Examination Report, Communication pursuant to Article 94(3) EPC, dated Sep. 8, 2008, for European Application No. EP 06816230.4, filed Oct. 2. 2006.

ISA/US PCT International Search Report and Written Opinion dated Feb. 6, 2007, for International Application No. PCT/US05/35533, filed Sep. 30. 2005.

ISA/US PCT international Preliminary Report on Patentability dated Apr. 3, 2007, for International Application No. PCT/US05/35533, filed Sep. 30. 2005.

ISA/US PCT International Search Report and Written Opinion dated Jan. 19, 2007, for International Application No. PCT/US06/38822, filed Oct. 2, 2006.

ISA/US PCT International Preliminary Report on Patentability dated Apr. 1, 2008, for International Application No. PCT/US06/38822, filed Oct. 2, 2006.

ISA/US PCT International Search Report and Written Opinion dated May 5, 2010, for International Application No. PCT/US10/20316, filed Jan. 7, 2010.

Intellectual Property Office of New Zealand, Examination Report dated May 18, 2009 for patent application No. 554514.

Baumgrass et al., 2004, "Substitution in Position 3 of Cyclosporin A Abolishes the Cyclophilin-mediated Gain-of-function Mechanism but Not Immunosuppression," *Journal of Biological Chemistry*, vol. 279(4):2470-2479.

Billich et al., 1995, "Mode of Action of SDZ NIM 811. A Nonimmunosuppressive Cyclosporin A Analog with Activity Against Human Immunodeficiency Virus (HIV) Type 1: Interference with HIV Protein-Cyclophilin A Interactions," *Journal of Virology*, vol. 69(4):2451-2461.

Cotler, Scott J., et al., Apr. 2003, "A Pilot Study of the Combination of Cyclosporin A and Interferon Alfacon-1 for the Treatment of Hepatitis C in Previous Nonresponder Patients," *Journal of Clinical Gastroenterology*, vol. 36(4):352-355.

Debio Pharm Press Release, New Data Presented on Debiopharm's Debio-25 at the 11$^{th}$ International Symposium on Hepatitis C Virus and Related Viruses in Heidelberg, Germany, Oct. 6, 2004.

Evers et al., 2003, "Synthesis of Non-Immunosuppressive Cyclophilin-Binding Cyclosporin A Derivatives as Potential Anti-HIV-1 Drugs," *Bioorganic & Medicinal Chemistry Letters*, vol. 13:4415-4419.

Hansson et al., 2004, "The Nonimmunosuppressive Cyclosporin Analogs NIM811 and UNIL025 Display Nanomolar Potencies on Permeability Transition in Brain Derived Mitochondria," *Journal of Bioenergetics and Biomembranes*, vol. 36(4):407-413.

Hopkins et al., 2009, "Safety, Plasma Pharmacokinetics, and Anti-Viral Activity of SCY-635 in Adult Patients with Chronic Hepatitis C virus Infection," *Journal of Hepatology*, vol. 50(Suppl. 1):S36 & 44$^{th}$ Annual meeting of the European Association for the Study of the Liver, Copenhagen, Denmark, Apr. 22-26, 2009.

Hubler et al.. 2000, Synthetic Routes to NEtXaa4-Cyclosporin A Derivatives as Potential Anti-HIV 1 Drugs, *Tetrahedron Letters*, vol. 41(37):7193-7196.

Inoue et al., 2000, "Hepatitis C Virus and Cyclosporin A," *Igaku no Ayumi*, vol. 193(12):951-954.

Inoue et al., 2003, "Combined Interferon Alpha2b and Cyclosporin A in the Treatment of Chronic Hepatitis C: Controlled Trial," *Journal of Gastroenterology*, Springer Verlag, Tokyo, JP, vol. 38(6):567-572.

Inoue et al., 2005, "Interferon Combined with Cyclosporin Treatment as an Effective Countermeasure Against Hepatitis C Virus Recurrence in Liver Transplant patients with End-Stage Hepatitis C Virus Related Disease." *Transplantation Proceedings*, vol. 37(2):1233-1234.

Kallen et al., 1997, "12 Cyclosporins: Recent Developments in Biosynthesis, Pharmacology and Biology, and Clinical Applications," *Biotechnology*, 2$^{nd}$ Ed. Completely Revised Edition, vol. 7, pp. 535-591.

Nakagawa et al., 2004, "Specific Inhibition of Hepatitis C Virus Replication by Cyclosporin A," *Biochem. Biophys. Res. Commun.*, vol. 313:42-47.

Peel et al., "The Discovery of Novel, Non-Immunosuppressive Cyclosporin Ethers, and Thioethers with Potent HCV Activity," AASLD Abstracts XP-002561933, *Hepatology*, vol. 48, No. 4. Suppl. S, Oct. 2008, p. 1167A, Abstract 1915.

Randall et al., 2003, "Clearance of Replicating Hepatitis C Virus Replicon RNAs in Cell Culture by Small Interfering RNAs," *PVAS*, vol. 100(1):235-240.

Ruegger et al., 1976, "Cyclosporin A, a Peptide Metabolite from *Trichoderma polysporum* (Link ex Pers.) *Rifai*, with a Remarkable Immunosuppressive Activity," *Helvetica Chimica Acta*, vol. 59(4) No. 112, pp. 1075-1092.

Sakamoto et al., 2004, "Specific Inhibition of Hepatitis C Virus Replication by Cyclosporin A," *Gastroenterology*, vol. 126(4). p. A-764 (Abstract T1674).

Schetter et al., 2004, "Toll-Like Receptors Involved in the Response to Microbial Pathogens: Development of Agonists for Toll-Like Receptor 9," *Current Opinion in Drug Discovery & Development*, vol. 7(2):204-210.

Scynexis Inc. Press Release, Scynexes' SCY-635 Demonstrates Clinically Relevant Single-agent Results in a Phase 1b Study in Adults with HCV (*Results presented in an oral presentation at EASL; Phase 2 studies to be initiated in 2H09*), Research Triangle Park, NC, USA, Apr. 24, 2009.

Shimotohno et al., 2004. "Inhibitory Role of Cyclosporin A and Its Derivatives on Replication of Hepatitis C Virus," American Transplant Congress, Abstract No. 648 (American Journal of Transplantation, 4(s8):1-653.

Simmonds. 2001, "The Origin and Evolution of Hepatitis Viruses in Humans," *Journal of General Virology*, vol. 82:693-712.

Simmonds, 2004, "Genetic Diversity and Evolution of Hepatitis C Virus—15 Years On," *Journal of General Virology*, vol. 85:3173-3188.

Summa, 2005, "VX-950 Vertex/Mitsubishi," *Current Opinion in Investigational Drugs*, vol. 6(8):831-837.

Takeda et al., 2003, "Toll-Like Receptors," *Annual Review Immunology*, vol. 21:335-376.

Wang et al., 2003, "Non-Nucleoside Analogue inhibitors Bind to an Allosteric Site on HCV NS5B Polymerase," *Journal of Biological Chemistry*, vol. 278( 11 ):9489-9495.

Watashi et al., 2003, "Cyclosporin A Suppresses Replication of Hepatitis C Virus Genome in Cultured Hepatocytes," *Hepatology*, vol. 38:1282-1288.

Watashi et al., 2005, "Cyclophilin B is a Functional Regulator of Hepatitis C Virus RNA Polymerase," *Molecular Cell*, vol. 19:111-122.

Watashi et al., 2005, "Current Approaches for Developing New Anti-HCV Agents and Analyses of HCV Replication Using Anti-IICV Agents," *Uirusu*, vol. 55(1):105-110.

Xia et al., 2005, "Inhibitory Effect of Cyclosporine A on Hepatitis B Virus Replication in Vitro and its Possible Mechanisms," *Hepatohiliary & Pancreatic Diseases International*, vol. 4(1):18-22.

EPO Communication pursuant to Article 94(3) EPC, dated Jul. 17, 2009, for European Patent Application No. 07795039.2.

Response to EPO Communication pursuant to Article 94(3) EPC, filed Apr. 28, 2010, for European Patent Application No. 07795039.2.

* cited by examiner

METHODS FOR THE TREATMENT AND PREVENTION OF OCULAR DISORDERS

This application is a continuation of U.S. patent application Ser. No. 12/301,210, filed Apr. 2, 2009 now U.S. Pat. No. 8,188,052, which is a National Stage of International Application No. PCT/US2007/011919, filed May 18, 2007, which claims the benefit of U.S. Provisional Application No. 60/802,208, filed May 19, 2006. The contents of all the above cited patent applications are hereby incorporated by reference herein in their entireties.

1 FIELD OF THE INVENTION

Provided herein are methods of using cyclosporin compounds and compositions in treatment or prevention of ocular diseases and disorders such as aqueous deficient dry-eye state, uveitis and phacoanaphylactic endophthalmitis. In certain aspects, the compounds for use in the methods provided herein are 3-alkylaminoalkyl, 3-dialkylaminoalkyl or 3-heterocyclylalkyl substituted cyclosporin compounds. In certain embodiments, the methods comprise administering to a subject in need thereof an amount of the compound provided herein effective to treat or prevent the ocular diseases and disorders such as aqueous deficient dry-eye state, uveitis and phacoanaphylactic endophthalmitis.

2 BACKGROUND

Dry-eye state may occur in a wide range of individuals, although it is more frequently seen in women, the elderly, and those with connective tissue disorders (e.g., rheumatoid arthritis, Sjögren's syndrome). Patients with dry eye commonly have complaints of ocular irritation or discomfort. As the name implies, dryness is the most frequently cited problem; patients may further report itching, burning, or a "sandy/gritty" foreign body sensation. Symptoms may be exacerbated by poor air quality, low humidity or extreme heat, and tend to be more prominent later in the day. Occasionally, patients report excess lacrimation, or epiphora, in association with the discomfort.

Uveitis, the inflammation of the uvea, is responsible for about 10% of the visual impairment in the United States. The uveal tract of the eye consists of the iris, ciliary body, and choroid. Inflammation of the overlying retina, called retinitis, or of the optic nerve, called optic neuritis, may occur with or without accompanying uveitis.

Uveitis is most commonly classified anatomically as anterior, intermediate, posterior, or diffuse. Anterior uveitis is localized primarily to the anterior segment of the eye and includes iritis and iridocyclitis. Intermediate uveitis, also called peripheral uveitis, is centered in the area immediately behind the iris and lens in the region of the ciliary body and pars plana, hence the alternate terms "cyclitis" and "pars planitis" are also used. Posterior uveitis signifies any of a number of forms of retinitis, choroiditis, or optic neuritis. Diffuse uveitis implies inflammation involving all parts of the eye, including anterior, intermediate, and posterior structures.

Phacoanaphylactic endophthalmitis is a human autoimmune disease. It is an inflammatory ocular condition secondary to rupture of the lens capsule, either traumatically or iatrogenically is also referred to as lens induced uveitis. Phacoanaphylaxis is a severe form of uveitis in which the lens is the causative antigen. The lens proteins are normally secluded by the lens capsule since before birth. When these proteins are released into the eye by injury or surgery or occasionally during cataract development, they can become intensely antigenic and incite an autoimmune response. If the response is moderate it is seen as a chronic uveitis. If it is very fast in progression the eye becomes severely inflamed in all segments. This latter response is named phacoanaphylaxis.

There is a continuing need to develop new and effective compounds to treat ocular diseases and disorders, such as dry eye, uveitis and phacoanaphylactic endophthalmitis.

Cyclosporins are a group of nonpolar cyclic oligopeptides with immunosuppressant, anti-inflammatory, and anti-parasitic properties. Cyclosporin A is a cyclosporin which is marketed in a topical ophthalmic emulsion formulation for the treatment of dry eye under the tradename Restasis. The insolubility of cyclosporins in water is an ongoing problem in the formulation of these compounds. In one aspect, the present invention seeks to provide cyclosporin derivatives having improved water solubility properties in comparison with cyclosporin A while maintaining useful properties for treating ocular diseases.

3 SUMMARY

Provided herein are methods for treating or preventing ocular diseases comprising administering to a subject in need thereof a therapeutically effective amount of a compound of general formula (I):

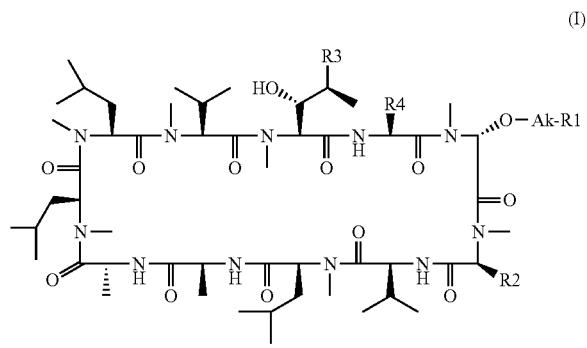

(I)

wherein:
Ak is alkylene;
$R^1$ is —$NR^5R^6$, in which $R^5$ and $R^6$ are each independently hydrogen or straight- or branched-chain alkyl comprising from one to six carbon atoms; or $R^5$ and $R^6$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by one to four groups which may be the same or different selected from alkyl, hydroxyl, amino, N-alkylamino and N,N-dialkylamino;
$R^2$ is isobutyl;
$R^3$ is (E)-2-butenyl-1 or n-butyl;
$R^4$ is ethyl, 1-hydroxyethyl, isopropyl or n-propyl;
or a pharmaceutically acceptable salt or solvate thereof.

4 DETAILED DESCRIPTION

Provided are methods of treating, preventing or ameliorating ocular diseases and disorders in a subject in need thereof. In one embodiment the present invention provides compounds of general formula (I) as defined above or pharmaceutically acceptable salts or solvates thereof, in the manufacture of a medicament for the treatment or prevention of ocular diseases. The methods and compositions are described in detail in the sections below.

4.1 Definitions

When referring to the compounds and complexes provided herein, the following terms have the following meanings unless indicated otherwise.

"Cyclosporin" refers to any cyclosporin compound known to those of skill in the art, or a derivative thereof. See, e.g., Ruegger et al., 1976, *Helv. Chim. Acta.* 59:1075-92; Borel et al., 1977, *Immunology* 32:1017-25; the contents of which are hereby incorporated by reference in their entireties. Exemplary compounds for use in the methods provided herein are cyclosporin derivatives. Unless noted otherwise, a cyclosporin described herein is a cyclosporin A, and a cyclosporin derivative described herein is a derivative of cyclosporin A.

"Alkyl" refers to monovalent saturated aliphatic hydrocarbyl groups, particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—$CH_2$—), ethylene (—$CH_2$ $CH_2$—), the propylene isomers (e.g., —$CH_2$ $CH_2$ $CH_2$— and —$CH(CH_3)CH_2$—) and the like.

"Amino" refers to the radical —$NH_2$.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, aryl, e.g. heteroaryl, and the like having from 1 to 5, and especially from 1 to 3 heteroatoms.

"Heterocycle" or "heterocyclic ring" refers to any heterocycle known to those of skill in the art. As used herein, a heterocycle can be a heteroaryl group or a cycloheteroalkyl group, as will be recognized by those of skill in the art. In certain embodiments, heterocyclyl refers to a 4, 5, or 6 membered saturated heterocyclic ring containing one or more heteroatoms in the ring.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Halogen" or "halo" refers to chloro, bromo, fluoro or iodo.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

It is to be understood that where reference is made in the present specification to the compounds of general formula, such reference is intended to include also the solvates, hydrates or salts with pharmaceutically acceptable acids or bases of compounds of general Formula (I) where appropriate.

"Sarcosine" refers to N-methyl glycine ($CH_3$ $NHCH_2CO_2H$).

"Solvate" refers to a compound provided herein or a salt thereof that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78:413-447, *Angew. Chem., Int. Ed. Engl.* 5:385-414 (errata: *Angew. Chem., Int. Ed. Engl.* 5:511); Prelog and Helmchen, 1982, *Angew. Chem.* 94:614-631, *Angew. Chem. Internat. Ed. Eng.* 21:567-583; Mata and Lobo, 1993, *Tetrahedron: Asymmetry* 4:657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture."

In certain embodiments, the compounds for use in the methods provided herein may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, provided herein are the stereoisomers of the compounds depicted herein upon treatment with base.

In certain embodiments, the compounds for use in the methods provided herein are "stereochemically pure." A stereochemically pure compound or has a level of stereochemical purity that would be recognized as "pure" by those of skill in the art. Of course, this level of purity will be less than 100%. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), including a human. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" refers to a compound provided herein. In certain other embodiments, the term "therapeutic agent" refers does not refer to a compound provided herein. A therapeutic agent is an agent which is known to be useful for, or has been or is currently being used for the treatment or prevention of a disorder or one or more symptoms thereof.

"Therapeutically effective amount" means an amount of a compound or complex or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in one embodiment, to ameliorating a disease or disorder that exists in a subject. In another embodiment, "treating" or "treatment" refers to ameliorating at least one physical parameter, which may be indiscernible by the subject. In yet another embodiment, "treating" or "treatment" refers to modulating the disease or disorder, either physically (e.g., stabilization of a discernible symptom) or physiologically (e.g., stabilization of a physical parameter) or both. In yet another embodiment, "treating" or "treatment" refers to delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" refers to a compound provided herein. In certain other embodiments, the term "prophylactic agent" does not refer a compound provided herein. In certain embodiments, a prophylactic agent is an agent which is known to be useful for, or has been or is currently being used to prevent or impede the onset, development, progression and/or severity of a disorder.

As used herein, the terms "prevent," "preventing" and "prevention" refer to the prevention of the recurrence, onset, or development of one or more symptoms of a disorder in a subject resulting from the administration of a therapy (e.g., a prophylactic or therapeutic agent), or the administration of a combination of therapies (e.g., a combination of prophylactic or therapeutic agents).

As used herein, the phrase "prophylactically effective amount" refers to the amount of a therapy (e.g., prophylactic agent) which is sufficient to result in the prevention of the development, recurrence or onset of one or more symptoms associated with a disorder (, or to enhance or improve the prophylactic effect(s) of another therapy (e.g., another prophylactic agent).

As used herein, the term "in combination" refers to the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" refers to a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent), and/or to administer said therapy less frequently, reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

4.2 Embodiments of the Invention

Provided herein are methods of treating, preventing or ameliorating ocular diseases and disorders such as aqueous deficient dry-eye state, uveitis and phacoanaphylactic endophthalmitis comprising administering in a subject in need thereof a compound of formula I. Without wishing to be limited to any particular theory of operation, it is believed that, in certain embodiments, the compounds act to enhance or restore lacrimal gland tearing in providing the desired therapeutic effect.

4.2.1 Compounds for Use in the Methods

Unless noted otherwise, the term "cyclosporin" as used herein refers to the compound cyclosporin A as known to those of skill in the art. See, e.g., Ruegger et al., 1976, *Helv. Chim. Acta.* 59:1075-92; Borel et al., 1977, *Immunology* 32:1017-25; the contents of which are hereby incorporated by reference in their entireties. The term "cyclosporin compound" refers to any cyclosporin compound with activity against ocular disease described herein, whether the compound is natural, synthetic or semi-synthetic.

In certain embodiments, Ak is —(CH$_2$)$_p$—, where p is 1, 2, 3 or 4; and/or R$^1$ is —NR$^5$R$^6$ and R$^5$ and R$^6$ are selected as follows a) R$^5$ and R$^6$ are each independently straight- or branched-chain alkyl comprising from one to six carbon atoms or b) R$^5$ and R$^6$, together with the nitrogen atom to which they are attached, form a saturated or unsaturated heterocyclic ring containing from five to six ring atoms, which ring may optionally contain another heteroatom selected from the group consisting of nitrogen, oxygen and sulfur. In certain embodiments, Ak is —CH$_2$CH$_2$—.

In certain embodiments R$^1$ is —NR$^5$R$^6$, in which R$^5$ and R$^6$ are each independently hydrogen or straight- or branched-chain alkyl comprising from one to six carbon atoms; or R$^5$ and R$^6$, together with the nitrogen atom to which they are attached, form a saturated or unsaturated heterocyclic ring containing from five to six ring atoms, which ring may optionally contain another heteroatom selected from the group consisting of nitrogen, oxygen and sulfur and may be optionally substituted by from one to four alkyl groups which may be the same or different.

In certain embodiments, R$^5$ and R$^6$ are both methyl. In certain embodiments, R$^5$ and R$^6$, together with the nitrogen atom to which they are attached, form a saturated heterocyclic ring containing six ring atoms, which ring may optionally contain another heteroatom selected from the group consisting of nitrogen, oxygen and sulfur. In a further embodiment, R$^5$ and R$^6$, together with the nitrogen atom to which they are attached, form an azetidinyl ring. In a still further embodiment, R$^5$ and R$^6$, together with the nitrogen atom to which they are attached, form a pyrrolidinyl ring. In certain embodiments, R$^5$ and R$^6$, together with the nitrogen atom to which they are attached, form a piperidinyl ring. In certain embodiments, R$^5$ and R$^6$, together with the nitrogen atom to which they are attached, form an N-methylpiperazinyl ring. In certain embodiments, R$^5$ and R$^6$, together with the nitrogen atom to which they are attached, form a morpholinyl ring. In certain embodiments, R$^5$ and R$^6$, together with the nitrogen atom to which they are attached, form a 2,6-dimethylmorpholinyl ring.

In particular embodiments, the cyclosporin compound differs from cyclosporin A at the third position, i.e. the N-methyl glycine position, known to those of skill in the art. In certain embodiments, the cyclosporin compound comprises a 3-alkylaminoalkyl, 3-N,N-dialkylaminoalkyl or 3-heterocyclylalkyl group. The cyclosporin compound can further comprise other cyclosporin modifications known to those of skill in the art.

In certain embodiments, the methods provided herein comprise administering to the subject a therapeutically or prophylactically effective amount of a cyclosporin compound of general Formula (I) above wherein B, X, R$^1$, R$^2$ and R$^3$ are as defined above, or a pharmaceutically acceptable salt or solvate thereof.

In certain embodiments, R$^3$ is (E)-2-butenyl-1. In certain embodiments R$^3$ is n-butyl.

In certain embodiments, R$^4$ is ethyl.

In a further embodiment Ak is (CH$_2$)$_p$ and p is two or three; R$^1$ is —NRSR$^6$; R$^5$ and R$^6$, which may be the same or different, are hydrogen or C$_{1-3}$alkyl; or R$^5$ and R$^6$, together with the nitrogen atom to which they are attached, form a saturated or unsaturated heterocyclic ring containing from four to six ring atoms, which ring may optionally contain another heteroatom selected from the group consisting of nitrogen and oxygen and may be optionally substituted by one or two groups which may be the same or different selected from methyl, hydroxyl and dimethylamino; R$^2$ is isobutyl; R$^3$ is (E)-2-butenyl-1; and R$^4$ is ethyl.

Among the compounds used in the methods provided herein, are the cyclosporin compounds listed below:

A 3-[2-(N,N-dimethylamino)ethoxy]cyclosporin.
B 3-[2-(azetidin-1-yl)ethoxy]cyclosporin.
C$_3$-[2-(pyrrolidin-1-yl)ethoxy]cyclosporin.
D 3-[2-(piperidin-1-yl)ethoxy]cyclosporin.
E 3-[2-(4-methylpiperazin-1-yl)ethoxy]cyclosporin.
F 3-[2-(morpholin-4-yl)ethoxy]cyclosporin.
G 3-[2-(2,6-dimethylmorpholin-4-yl)ethoxy]cyclosporin.
H 3-[2-(3-hydroxypyrrolidin-1-yl)ethoxy]cyclosporin.
I 3-{2-[(4-dimethylamino)piperidin-1-yl]ethoxy}cyclosporin.
J 3-[2-(4-hydroxypiperidin-1-yl)ethoxy]cyclosporin.
K 3-[2-(imidazol-1-yl)ethoxy]cyclosporin.
L 3-[2-(N-methylamino)ethoxy]cyclosporin.
M 3-[2-(N-isopropyl-N-methylamino)ethoxy]cyclosporin.
N 3-[2-(aminopropoxy)]cyclosporin.

The Compound Letters A to N are used hereafter.

Salts of Compounds of formula (I) are novel and as such form a further feature of the present invention. In one embodiment the salt is selected from the group consisting of hydrochloride, sulfate, phosphate, carbonate, acetate, tartrate, citrate, maleate, succinate, lactate, stearate, propionate, benzoate, fumarate, hippurate, gluconate, ascorbate, adipate, glutamate, mesylate, tosylate, oleate, laurylsulphate, hydrobromide and nitrate.

In certain embodiments, the cyclosporin derivatives provided herein have an optimized potency for immune suppression. The immunomodulation potency relative to cyclosporin A can be measured in an assay of the mixed lymphocyte response (MLR). The assay is known to one of skill in the art, for example, see, U.S. Pat. No. 6,946,465. Lymphocytes from rats, mouse or human could be used in the assay. In certain embodiments, the cyclosporin derivatives provided herein are equipotent to cyclosporin A in the MLR assay. In certain embodiments, the cyclosporin derivatives provided herein are from about 1 to about 5000, from about 10 to about 3000, from about 50 to about 2000, from about 70 to about 1000, from about 100 to about 500, from about 150 to about 300 fold less potent than cyclosporin A. In certain embodiments, the cyclosporin derivatives provided herein are from about 10 to about 100 or about 100 to about 5000 fold less potent than cyclosporin A. In certain embodiments, the cyclosporin derivatives provided herein are from about 2 to about 100, from about 2 to about 80, from about 2 to about 65, from about 2 to about 50, from about 2 to about 30, from about 2 to about 20, from about 2 to about 10, from about 2 to about 9, from about 2 to about 7 or from about 2 to about 5 fold less potent than cyclosporin A. In certain embodiments, the cyclosporin derivatives provided herein are about 1, 5, 10, 15, 25, 50, 100, 150, 200, 250, 300, 350, 400, 450, 500 or 1000 fold less potent than cyclosporin A.

Other cell-based assays can also be used to determine the activity against production of specific pro-inflammatory cytokines, including, IL-1, IL-2, IL-4, IL-6, TNF-α, interferons and TGF-β. In certain embodiments, the cyclosporin derivatives herein provide clinical benefit in the treatment of the dry eye or uveitis by down regulating cytokines.

In certain embodiments, the cyclosporin derivatives provided herein have solubility that is useful for creating an optimized formulation for delivery and release of the compound in eye. In certain embodiments, the cyclosporin derivatives provided herein have improved solubility over cyclosporin A. In certain embodiments, the cyclosporin derivatives have aqueous solubility from about 0.001 to about 5 mM, about 0.005 to about 3 mM, about 0.007 to about 1 mM, about 0.01 to about 0.5 mM, about 0.02 to about 0.3 mM, about 0.05 to about 0.1 mM, about 0.06 to about 0.6 mM, about 0.08 to about 0.5 mM or about 0.1 to about 1 mM.

In certain embodiments, the cyclosporin derivatives provided herein have an improved safety profile relative to cyclosporin. The safety profile can be determined in a variety of test models including acute and chronic animal toxicology models. Potential human toxicity could also be determined using human-cell-based assays known as cytotoxicity assays. Cytotoxicity can be evaluated in various cell types using a variety of indicators and reporters, for example, see, Guidance Document on Using In Vitro Data to Estimate In Vivo Starting Doses for Acute Toxicity, (NIH Publication No. 01-4500). In certain embodiments, the compounds for use in the methods provided herein are from about 2 to about 10, from about 3 to about 8, from about 2 to about 6, from about 2 to about 5, from about 2 to about 3 fold less active than cyclosporin in a cytotoxicity assay.

In certain embodiments, the compound is in a pure form. Purity can be any purity known to those of skill in the art such as absolute purity, stereochemical purity or both. In certain embodiments, the compound is at least 80%, 85%, 90%, 91%, 92%, 93%, 94%, 95%, 96%, 97%, 98% or 99% pure. In certain embodiments, the compound is at least 90% pure. In further embodiments, the compound is at least 98% pure. Methods of purifying these compounds are described below.

Compounds of Formula (I) or pharmaceutically acceptable salts thereof are known in the literature or may be prepared by the adaptation of known methods, for example as described in U.S. Pat. Nos. 6,583,265 or International Patent publication Nos. WO99/65933, WO99/67280, the contents of which are incorporated herein by reference.

4.2.2 Pharmaceutical Compositions and Methods of Administration

The cyclosporin compounds for use in the methods provided herein are useful for treatment of ocular diseases.

The methods provided herein use pharmaceutical compositions containing at least one compound of general Formula (I), if appropriate in the salt form, either used alone or in the form of a combination with one or more compatible and pharmaceutically acceptable carriers, such as diluents or adjuvants, or in combination with other active ingredients. In clinical practice the cyclosporin compounds for use in the methods provided herein may be administered by any conventional route, including but not limited to topically orally, parenterally or by inhalation (e.g. in the form of aerosols). In one embodiment, the cyclosporin compounds for use in the methods provided herein are administered orally.

Use may be made, as solid compositions for oral administration, of tablets, pills, hard gelatin capsules, powders or granules. In these compositions, the active product provided herein is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavouring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In certain embodiments, water is a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmocopia (USP)SP(XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are, in certain embodiments, anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in certain embodiments, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In one embodiment, the pharmaceutical compositions or single unit dosage forms are sterile and in suitable form for administration to a subject, such as an animal subject, or a mammalian subject, and such as a human subject.

A pharmaceutical composition provided herein is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral and intra-synovial. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of ocular disease may contain larger amounts of one or more of the active ingredients it comprises than a dosage form used in the maintenance treatment of the disease. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., *Remington's Pharmaceutical Sciences,* 20th ed., Mack Publishing, Easton Pa. (2000).

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms provided herein comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms provided herein have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active cyclosporin.

4.2.2.1 Transdermal, Topical & Mucosal Dosage Forms

In certain embodiments, provided herein are transdermal, topical, and mucosal dosage forms. Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 20th ed., Mack Publishing, Easton Pa. (2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 20th ed., Mack Publishing, Easton Pa. (2000).

Depending on the specific tissue to be treated, additional components may be used prior to, in conjunction with, or subsequent to treatment with active ingredients provided herein. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethylacetamide; dimethylformamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

4.2.2.2 Pharmaceutical Compositions for Ophthalmic Administration

The methods provided herein use pharmaceutical compositions containing at least one compound of general Formula (I), if appropriate in the salt form, either used alone or in the form of a combination with one or more compatible and pharmaceutically acceptable carriers, such as diluents or adjuvants, or in combination with other active ingredient, such as another agent useful in treatment of ocular diseases. In clinical practice the pharmaceutical compositions containing cyclosporin compounds for use in the methods provided herein may be administered in any form suitable for ocular drug administration, e.g., as a solution, suspension, ointment, gel, liposomal dispersion, colloidal microparticle suspension, injection, such as intraocular injection or subconjuctival injection or the like, or in an ocular insert, e.g., in an optionally biodegradable controlled release polymeric matrix. In certain embodiments, the compositions are formulated as aqueous solutions. In other embodiments, the compositions are suspensions, viscous or semi-viscous gels, or other types of solid or semi-solid compositions.

A variety of carriers may be used in the formulations, including, but not limited to water, mixtures of water and water-miscible solvents, such as $C_1$-$C_7$-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, cross-linked polyacrylic acid, such as neutral Carbopol, or mixtures of those polymers. The concentration of the carrier is, typically, from 1 to 10000 times the concentration of the active ingredient.

Additional ingredients that may be included in the formulation include tonicity enhancers, preservatives, solubilizers, non-toxic excipients, demulcents, sequestering agents, pH adjusting agents, co-solvents and viscosity building agents.

In certain embodiments, for the adjustment of the pH, for example, to a physiological pH, buffers are used. The pH is typically maintained within the range of about 4.0 to 8.0, about 4.0 to 6.0 or about 6.5 to 7.5. In certain embodiments, the pH is maintained at about 6, 6.3, 6.5, 6.7, 7.0, 7.2 or 7.5. Suitable buffers may be added, such as acetate, ascorbate, boric acid, sodium borate, potassium citrate, citric acid, sodium bicarbonate, gluconate, lactate, phosphate, propionate, TRIS, and various mixed phosphate buffers (including combinations of $Na_2HPO_4$, $NaH_2PO_4$ and $KH_2PO_4$) and mixtures thereof. The amount of buffer substance added is, for example, that necessary to ensure and maintain a physiologically tolerable pH range. Generally, buffers will be used in amounts ranging from about 0.05 to 3% by weight, about 0.07 to 2.5% by weight, about 0.1 to 2% by weight, about 0.5 to 2% by weight or about 1 to 2% by weight. In certain embodiments, the amount of buffer is about 0.05, 0.1, 0.5, 1, 1.5, 2, 2.3 or 3% by weight of the formulation.

In certain embodiments, the compositions contain tonicity enhancing agents selected from ionic and non-ionic compounds. Ionic compounds for use herein include, but are not limited to alkali metal or alkaline earth metal halides, such as, for example, $CaCl_2$, KBr, KCl, LiCl, NaI, NaBr or NaCl, or boric acid. Non-ionic tonicity enhancing agents are, for example, urea, glycerol, sorbitol, mannitol, propylene glycol, or dextrose. The compositions provided herein contain, for example, sufficient tonicity enhancing agent to impart to the ready-for-use ophthalmic composition an osmolality of approximately from about 50 to 1000 mOsmol, from about 100 to 500 mOsmol, from about 200 to 400 mOsmol, from about 280 to 350 mOsmol or from about 230 to 320 mOsmol.

In certain embodiments, the compositions provided herein contain a preservative. Examples of preservatives are quaternary ammonium salts, such as cetrimide, benzalkonium chloride or benzoxonium chloride, alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sodium perborate, Germal®II or sorbic acid. In certain embodiments, the preservative is cetrimide, benzalkonium chloride, benzoxonium chloride or parabens. Where appropriate, a sufficient amount of preservative is added to the ophthalmic composition to ensure protection against secondary contaminations during use caused by bacteria and fungi.

In another embodiment, the topical formulations provided herein do not include a preservative. Such formulations would be useful for patients who wear contact lenses, or those who use several topical ophthalmic drops and/or those with an already compromised ocular surface wherein limiting exposure to a preservative may be more desirable.

The topical formulation provided herein can additionally contain a solubilizer. A solubilizer suitable for use in the composition is for example selected from tyloxapol, fatty acid glycerol polyethylene glycol esters, fatty acid polyethylene glycol esters, polyethylene glycols, glycerol ethers, a cyclodextrin (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin or panosyl-cyclodextrin), polysorbate 20, polysorbate 80, olive oil, castor oil, arachis oil, mineral oil or mixtures of those compounds. In certain embodiments, the solubilizer is a reaction product of castor oil and ethylene oxide, for example the commercial products Cremophor® EL or Cremophor RH40®. Reaction products of castor oil and ethylene oxide are known to be particularly good solubilizers that are tolerated well by the eye. In other embodiments, the solubilizer is selected from tyloxapol and from a cyclodextrin. The concentration of the solubilized used herein depends especially on the concentration of the active ingredient. The amount added is typically sufficient to solubilize the active ingredient. For example, the concentration of the solubilizer is from 0.1 to 5000 times the concentration of the active ingredient.

The formulations can further contain non-toxic excipients, such as, for example, petroleum jelly, dimethyl sulfoxide, Miglyol 182 (commercially available from Dynamit Nobel Kay-Fries Chemical Company, Mont Vale, N.J.), an alcohol (e.g. ethanol, n-propyl alcohol, or isopropyl alcohol), liposomes or liposome-like products or a silicone fluid, emulsifiers, wetting agents or fillers, such as, for example, the polyethylene glycols designated 200, 300, 400 and 600, or Carbowax designated 1000, 1500, 4000, 6000 and 10000. Other excipients that may be used if desired are listed below but they are not intended to limit in any way the scope of the possible excipients. They are complexing agents, such as disodium-EDTA or EDTA, antioxidants, such as ascorbic acid, acetylcysteine, cysteine, sodium hydrogen sulfite, butyl-hydroxyanisole, butyl-hydroxytoluene or α-tocopherol acetate; stabilizers, such as a cyclodextrin, thiourea, thiosorbitol, sodium dioctyl sulfosuccinate or monothioglycerol, vitamin E and vitamin E derivatives, such as Vitamin E Tocopherol Polyethylene Glycol 1000 Succinate (TPGS); or other excipients, such as, for example, lauric acid sorbitol ester, triethanol amine oleate or palmitic acid ester. In certain embodiments, the excipients are complexing agents, such as disodium-EDTA and stabilizers, such as a cyclodextrin. The amount and type of excipient added is in accordance with the particular requirements and is generally in the range of from approximately 0.0001 to approximately 90% by weight.

Other compounds may also be added to the formulations provided herein to increase the viscosity of the carrier. Examples of viscosity enhancing agents include, but are not limited to: cellulosic polymers such as methylcellulose (MC), hydroxyethylcellulose (HEC), hydroxypropylcellulose (HPC), hydroxypropyl-methylcellulose (HPMC), and sodium carboxymethylcellulose (NaCMC), and other swellable hydrophilic polymers such as polyvinyl alcohol (PVA), hyaluronic acid or a salt thereof (e.g., sodium hyaluronate), chondroitin sulfate and its salts, dextrans and crosslinked acrylic acid polymers commonly referred to as "carbomers" (and available from B.F. Goodrich as Carbopol® polymers). In certain embodiments, amount of any thickener is such that a viscosity in the range of about 15 cps to 25 cps is provided, as a solution having a viscosity in the aforementioned range is generally considered optimal for both comfort and retention of the formulation in the eye.

In certain embodiments, the compositions provided herein comprise a compound provided herein, carmellose sodium in purified water as a lubricant (purified water as a lubricant), hypotonic, borate buffer, sodium chloride, potassium chloride, sodium bicarbonate, calcium chloride, magnesium chloride and sodium phosphate. In certain embodiments, the compositions provided herein comprise a compound provided herein mineral oil and lanolin. In certain embodiments, the compositions provided herein comprise a compound provided herein, buffered solution, isotonic aqueous solution, citrate buffer, sodium chloride, edetate disodium and polyquad polyquaternium. In certain embodiments, the compositions provided herein comprise a compound provided herein, sodium chloride, boric acid, potassium chloride, calcium chloride, magnesium chloride, purified water, and stabilized oxychloro complex.

4.2.3 Methods of Treatment

Provided herein are methods for treating or preventing ocular disease, such as dry eye, uveitis and phacoanaphylactic endophthalmitis in a subject in need of such treatment.

Although it appears that dry eye may result from a number of unrelated pathogenic causes, all presentations of the complication share a common effect, which is the breakdown of the pre-ocular tear film, which results in dehydration of the exposed outer surface and many of the symptoms outlined above. In certain embodiments, symptoms of dry eye include feeling of dryness, and persistent irritation such as is often caused by small bodies lodging between the eye lid and the eye surface. In severe cases, vision may be substantially impaired. Dry eye disease includes, but is not limited to keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies (including vitamin), pharmacologic side effects, eye stress and glandular and tissue destruction, environmental exposure to smog, smoke, excessively dry air, airborne particulates, autoimmune and other immunodeficient disorders. The methods provided herein treat or prevent one or more diseases of dry eye.

In certain embodiments, provided herein are methods for treatment or prevention of uveitis. In certain embodiments, uveitis is anterior, intermediate, posterior, or diffuse uveitis. Anterior uveitis is localized primarily to the anterior segment of the eye and includes iritis and iridocyclitis. Intermediate uveitis, also called peripheral uveitis, is centered in the area immediately behind the iris and lens in the region of the ciliary body and pars plana. Posterior uveitis signifies any of a number of forms of retinitis, choroiditis, or optic neuritis. Diffuse uveitis implies inflammation involving all parts of the eye, including anterior, intermediate, and posterior structures. The symptoms of uveitis can vary depending on the location of the uveitis; acute and severe symptoms are generally more common in anterior uveitis and can include: eye pain, eye redness, photophobia, blurred or decreased vision and blindness. Other symptoms include "floaters" which are small specks or clouds that move with the field of vision, chronic flare in the eye, band keratopathy, secondary glaucoma and posterior subcapsular cataracts.

In certain embodiments, provided herein are methods for treatment or prevention of phacoanaphylactic endophthalmitis. In certain embodiments, provided herein are methods for treatment or prevention of phacoanaphylaxis, which is a severe form of uveitis.

4.2.4 Dosage and Unit Dosage Forms

In human therapeutics, the doctor will determine the dosage regimen which he considers most appropriate according to a preventive or curative treatment and according to the age, weight, stage of the disease and other factors specific to the subject to be treated. In certain embodiments, dose rates are from about 0.001 to about 1000 mg per day for an adult. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day, about 25 to 200 mg per day, about 50 to about 500 mg per day per adult. In certain embodiments, doses are about 0.001 to about 500 mg per day, about 0.001 to about 100 mg per day, from about 0.005 to about 50 mg per day, from about 0.01 to 10 mg per day, from about 0.03 to 1 mg per day, from about 0.05 to 1 mg per day, from about 0.06 to 1 mg per day, from about 0.08 to 1 mg or from about 0.1 to 1 mg per day for an adult. In certain embodiments, doses are about 0.001 mg, 0.005 mg, 0.01 mg, 0.02 mg, 0.03 mg, 0.04 mg, 0.05 mg, 0.06 mg, 0.07 mg, 0.08 mg, 0.09 mg, 0.1 mg, 0.3 mg, 0.5 mg, 1 mg, 5 mg, 10 mg, 15 mg, 20 mg, 25 mg, 30 mg, 35 mg, 40 mg, 45 mg, 50 mg, 60 mg, 70 mg, 80 mg or 100 mg per day per adult.

The amount of the compound or composition provided herein which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

Exemplary doses of a composition include milligram or microgram amounts of the active compound per kilogram of subject or sample weight (e.g., from about 0.1 micrograms per kilogram to about 50 milligrams per kilogram, from about 0.5 micrograms per kilogram to about milligrams per kilogram, from about 0.1 micrograms per kilogram to about 10 milligrams per kilogram, from about 1 micrograms per kilogram to about 5 milligrams per kilogram, from about micrograms per kilogram to about 5 milligrams per kilogram, from about 100 micrograms per kilogram to about 2.5 milligrams per kilogram, or from about 100 microgram per kilogram to about 1 milligrams per kilogram). In certain embodiments, the doses are about 10 micrograms per kilogram to about 50 milligrams per kilogram, about 100 micrograms per kilogram to about milligrams per kilogram, or about 100 microgram per kilogram to about 10 milligrams per kilogram of subject or sample weight. For compositions provided, the dosage administered to a subject is typically 0.140 mg/kg to 3 mg/kg of the subject's body weight, based on weight of the active compound. In some embodiments, the dosage administered to a subject is between 0.20 mg/kg and 2.00 mg/kg, or between 0.30 mg/kg and 1.50 mg/kg of the subject's body weight. In certain embodiments, for compositions provided herein, the dosage administered to a subject is from about 0.0001 mg/kg to 0.01 mg/kg of the subject's body weight, based on weight of the active compound. In certain embodiments, for compositions provided herein, the dosage administered to a subject is from about 0.0005 mg/kg to 0.01 mg/kg of the subject's body weight, based on weight of the active compound. In certain embodiments, for compositions provided herein, the dosage administered to a subject is 0.140 mg/kg to 3 mg/kg of the subject's body weight, based on weight of the active compound. In certain embodiments, the dosage administered to a subject is from about 0.0001 mg/kg to about 0.01 mg/kg, about 0.0005 mg/kg to about 0.001 mg/kg, from about 0.001 mg/kg to about 0.01 mg/kg, about 0.20 mg/kg and 2.00 mg/kg, or between 0.30 mg/kg and 1.50 mg/kg of the subject's body weight. In certain embodiments, the dosage administered to a subject is about 0.001 mg/kg, such that for a patient weighing about 60 kg, the amount of the compound of formula I administered is about 0.006 mg per dose.

In certain embodiments, the recommended daily dose range of a composition provided herein for the conditions described herein lie within the range of from about 0.0005 mg to about 0.1 mg per day or from about 0.1 mg to about 1000 mg per day, given as a single once-a-day dose or as divided doses throughout a day. In one embodiment, the daily dose is administered twice daily in equally divided doses. In one embodiment, a daily dose range is from about 10 mg to about 200 mg per day, about 10 mg and about 150 mg per day, or about 25 and about 100 mg per day. In another embodiment, a daily dose range is from about 0.0001 mg to about 0.01 mg per day, in another embodiment, a daily dose range is from about 0.0005 mg to about 0.005 mg per day, or in another embodiment, a daily dose range is from about 0.001 mg to about 0.05 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In a specific embodiment, the dosage of the composition provided herein, based on weight of the active compound, administered to prevent, treat, manage, or ameliorate a disorder, or one or more symptoms thereof in a subject is about 0.0001 mg/kg, 0.0005 mg/kg, 0.0007 mg/kg, 0.0009 mg/kg, 0.001 mg/kg, 0.0012 mg/kg, 0.0015 mg/kg, 0.0017 mg/kg, 0.002 mg/kg, 0.0025 mg/kg, 0.003 mg/kg, 0.0035 mg/kg, 0.004 mg/kg, 0.005 mg/kg, 0.01 mg/kg, 0.1 mg/kg, 1 mg/kg or more of a subject's body weight. In another embodiment, the dosage of the composition provided herein is administered to prevent, treat, manage, or ameliorate a disorder, or one or more symptoms thereof in a subject is a unit dose of from about 0.0001 mg to about 100 mg, 0.0005 mg to 50 mg, 0.0008 mg to 25 mg, 0.001 mg to 10 mg, 0.0013 mg to 10 mg, 0.0015 mg to 10 mg, 0.0018 mg to 10 mg, 0.002 mg to 10 mg, 0.005 mg to 10 mg, 0.015 mg to mg, 0.01 mg to 1 mg or 0.1 mg to 1 mg.

In certain embodiments, administration of the same composition provided herein may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided are unit dosages comprising a compound provided herein, or a pharmaceutically acceptable salt thereof, in a form suitable for administration. Such forms are described in detail above. In particular embodiments, the unit dosages comprise about 0.001, 0.005, 0.006, 0.007, 0.008, 0.009, 0.01, 0.015, 0.02, 0.025, 0.03, 0.05, 0.1, 1, 5, 10, 25, 50 or 100 mg active ingredient. Such unit dosages can be prepared according to techniques familiar to those of skill in the art.

4.2.5 Combination Therapy

In certain embodiments, provided herein are methods of treatment of prevention that comprise the administration of a second agent effective for the treatment or prevention of ocular diseases and disorders such as aqueous deficient dry-eye state, uveitis or phacoanaphylactic endophthalmitis in a subject in need thereof. The second agent can be any agent known to those of skill in the art to be effective for the treatment or prevention of dry-eye, uveitis or phacoanaphylactic endophthalmitis. The second agent can be a second agent presently known to those of skill in the art, or the second agent can be second agent later developed for the treatment or prevention of dry-eye, uveitis and/or phacoanaphylactic endophthalmitis. In certain embodiments, the second agent is presently approved for the treatment or prevention of dry eye, uveitis and/or phacoanaphylactic endophthalmitis.

In certain embodiments, the second therapeutically active agent could be any drug which might be useful in treating the symptoms of dry eye, uveitis and/or phacoanaphylactic endophthalmitis, or any of its underlying causes. In addition, the second therapeutically active agent could be any drug which is useful in preventing or treating any disease which might occur simultaneously to dry eye, uveitis and/or phacoanaphylactic endophthalmitis disease, whether or not the disease is related. In certain embodiments, the second therapeutically active agent could be a drug which is used in topical ophthalmic compositions which might cause, contribute to, or aggravate ocular diseases contemplated herein as a side effect of its use. In this aspect, the methods provided herein are useful in reducing or eliminating said side effect.

One class of useful second therapeutically active agents in the methods for treating ocular disease provided herein is nucleotide purinergic receptor agonists such as uridine 5'-triphosphate, dinucleotides, cytidine 5'-diphosphosphate, adenosine 5'-diphosphate, $P^1$-(cytidine 5'-)-P-(uridine 5'-)tetraphosphates, $P^1$, $P^4$-di(uridine 5')-tetraphosphates, or their therapeutically effective analogues or derivatives, which may affect tear secretion, particularly the mucous layer of tears, and thus may have potential in treating dry eye disease. These compounds are described in the following patents, all of which are incorporated herein by reference: U.S. Pat. Nos. 6,555,675; 6,548,658; 6,436,910; 6,348,589; 6,331,529; 6,323,187; 6,319,908; and 5,900,407.

Another useful class of compounds that are useful as second therapeutically active agents in the methods for treating ocular disease provided herein is nicotinic receptor agonists such as nicotine and its analogs, trans-metanicotine and its analogs, epibatidine and its analogs, pyridol derivatives, piperidine alkaloids such as lobeline and its analogs, certain para-alkylthiophenol derivatives, and imidacloprid and its analogs. These compounds are believed to stimulate secretion of mucin by the conjunctival goblet cells, and thus may be useful in treating dry eye, as disclosed in U.S. Pat. No. 6,277,855, which is incorporated herein by reference.

Another useful class of second therapeutically active agents in the methods for treating ocular disease provided herein is tetracycline, derivatives or analogues of tetracycline, or chemically modified tetracycline. These compounds are believed to have potential in correcting delayed tear clearance, as described in U.S. Pat. No. 6,455,583 B1, incorporated herein by reference, which is related to some cases of dry eye.

Another class of compounds that are useful as second therapeutically active agents in the methods for treating ocular disease provided herein is corticosteroids such as methylprednisolone sodium succinate, prednisolone acetate, prednisolone sodium phosphate, fluorometholone, fluorometholone acetate, dexamethasone sodium phosphate, hydroxymethylprogesterone, rimexolane, budesonide, and tixocortol pivalatein, which are believed to be useful in treating dry eye as disclosed in U.S. Pat. No. 6,153,607, incorporated herein by reference.

Another class of compounds which are useful as second therapeutically active agents in the methods for treating ocular disease provided herein is products of human lacrimal gland acinar epithelia such as growth factors or cytokines including the transforming growth factor beta (TGFβ), which are disclosed to be useful in treating dry eye in U.S. Pat. No. 5,652,209, incorporated herein by reference.

Another class useful second therapeutically active agents in the methods for treating ocular disease provided herein is androgens or androgen analogues such as 17α-methyl-17β-hydroxy-2-oxa-5α-androstan-3-one, testosterone or testosterone derivatives, 4,5α-dihydrotestosterone or derivatives, 17β-hydroxy-5α-androstane and derivatives, 19-nortestosterone or derivatives, and nitrogen-substituted androgens, which are taught to be useful in treating dry eye disease in the following patents which are incorporated herein by reference, U.S. Pat. Nos. 6,107,289; 5,958,912; 5,688,765; and 5,620,921.

In certain embodiments, the second therapeutically active agents in the methods for treating ocular disease provided herein are topical corticosteroids, including, but not limited to prednisone and triamcinolone acetonide; cycloplegic agents such as cyclopentolate and homatropine hydrobromide and immunosuppressive drugs, such as methotrexate, cyclosporin A, cyclophosphamide and chlorambucil.

Another class useful second therapeutically active agents in the methods for treating ocular disease provided herein are antibiotics, including, but not limited to macrolides (e.g. rapamycin, tobramycin, ascomycin, azalides such as azithromycin); oxazolidinones (e.g. linezolid, eperezolid); quinolones (e.g. ofloxacin, norfloxacin, ciprofloxacin, lomefloxacin), gentamicin, and pilocarpine.

Other useful second therapeutically active agents in the methods for treating ocular disease provided herein are selected from cyclosporin A, cyclosporin B, cyclosporin C, cyclosporin D, and cyclosporin G.

In certain embodiments, the second agent can be formulated or packaged with the cyclosporin derivatives provided herein. Of course, the second agent will only be formulated with the cyclosporin derivative provided herein when, according to the judgment of those of skill in the art, such co-formulation should not interfere with the activity of either agent or the method of administration. In certain embodiment, the cyclosporin derivative provided herein and the second agent are formulated separately. They can be packaged together, or packaged separately, for the convenience of the practitioner of skill in the art.

The dosages of the second agents are to be used in the combination therapies provided herein. In certain embodiments, dosages lower than those which have been or are currently being used to prevent or treat the diseases contemplated herein are used in the combination therapies provided herein. The recommended dosages of second agents can obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J., which are incorporated herein by reference in its entirety.

In various embodiments, the therapies (e.g., the cyclosporin derivative provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In certain embodiments, two or more therapies are administered within the same patent visit.

In certain embodiments, the cyclosporin derivative provided herein and the second agent are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least 1 day, 2 days, 3 days, 5 days, 10 days, 15 days, 30 days, 45 days, 2 months, 75 days, 3 months, or 6 months.

In certain embodiments, a cyclosporin derivative provided herein and a second agent are administered to a patient, such as a mammal, including a human, in a sequence and within a time interval such that the cyclosporin derivative can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the cyclosporin derivative and the second active agent exert their effects at times which overlap. Each second active agent can be administered separately, in any appropriate form and by any suitable route. In other embodiments, the cyclosporin derivative is administered before, concurrently or after administration of the second active agent.

In various embodiments, the cyclosporin derivative and the second agent are administered less than about 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In other embodiments, the cyclosporin derivative and the second agent are administered concurrently.

In other embodiments, the cyclosporin derivative and the second agent are administered at about 2 to 4 days apart, at about 4 to 6 days apart, at about 1 week part, at about 1 to 2 weeks apart, or more than 2 weeks apart.

In certain embodiments, the cyclosporin derivative and the second agent are cyclically administered to a patient. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improve the efficacy of the treatment.

In certain embodiments, the cyclosporin derivative and the second active agent are administered in a cycle of less than about 3 weeks, about once every two weeks, about once every 10 days or about once every week. One cycle can comprise the administration of a cyclosporin derivative and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the cyclosporin derivative can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the cyclosporin derivative. In one embodiment, a cyclosporin derivative is administered concurrently with one or more second agents in the same pharmaceutical composition. In another embodiment, a cyclosporin derivative is administered concurrently with one or more second agents in separate pharmaceutical compositions. In still another embodiment, a cyclosporin derivative is administered prior to or subsequent to administration of a second agent. Also contemplated is administration of a cyclosporin derivative and a second agent by the same or different routes of administration, e.g., oral and parenteral. In certain embodiments, when a cyclosporin derivative is administered concurrently with a second agent that potentially produces adverse side effects including, but not limited to, toxicity, the second active agent can advantageously be administered at a dose that falls below the threshold that the adverse side effect is elicited.

4.2.6 Kits

In certain embodiments, provided are kits for use in methods of treatment or prophylaxis of ocular diseases. The kits can include a pharmaceutical compound or composition provided herein and instructions providing information to a health care provider regarding usage for treating or preventing ocular disease. Instructions may be provided in printed form or in the form of an electronic medium such as a floppy disc, CD, or DVD, or in the form of a website address where such instructions may be obtained. A unit dose of a compound or composition provided herein can include a dosage such that when administered to a subject, a therapeutically or prophylactically effective plasma level of the compound or composition can be maintained in the subject for at least 1 day. In some embodiments, a compound or composition provided herein can be included as a sterile aqueous pharmaceutical composition or dry powder (e.g., lyophilized) composition. In one embodiment, the compound is according to Formula (I).

In some embodiments, suitable packaging is provided. As used herein, "packaging" refers to a solid matrix or material customarily used in a system and capable of holding within fixed limits a compound or composition provided herein suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Kits provided herein may also comprise, in addition to the compound or composition provided herein, second agents or compositions comprising second agents for use with compound or composition as described in the methods above.

The following Examples illustrate the preparation of compositions used in the methods of the present invention. Specifically documented is the 7 step synthesis of 3-[2-(pyrrolidin-1-yl)ethoxy]cyclosporin (compound C) from cyclosporin A. Also shown is the synthesis of the phosphate salt of compound C. Compounds A, B, D, E, F, and G, along with their phosphate salts, can be synthesized in an analogous manner using different amines during the penultimate reductive amination step.

Numerous modifications and variations of the claimed subject matter are possible in view of the teachings herein and, therefore, are within the scope of the claimed subject matter.

5 EXAMPLES

Example E1

To a solution of [3'-acetoxy-N-methyl-Bmt][1][(R)-2'-(2-pyrrolidin-1-yl)ethoxy-Sar][3] cyclosporin A (150 mg) in methanol (10 mL) was added 25 wt % sodium methoxide in methanol (0.04 mL) and the resulting mixture was stirred at room temperature for 24 hours under nitrogen. Methanol was removed under reduced pressure and the residue was diluted with ethyl acetate, washed with saturated ammonium chloride, brine, and dried over anhydrous sodium sulfate. After solvent removal, the residue was purified using preparative liquid chromatography to yield 33 mg of 3-[2-(pyrrolidin-1-yl)ethoxy]cyclosporin (Compound C). $^1$H NMR peaks at 5.89, 7.10, 7.15, 7.64 and 7.96 ppm. LCMS (ESI): calculated for $C_{68}H_{122}N_{12}O_{13}$: 1314. found 1315.2 (M+H)$^+$.

By proceeding in a similar manner the following compounds were also prepared:

| Compound | $^1$H NMR |
|---|---|
| A | 6.00, 7.16, 7.23, 7.71, 7.97; |
|   | phosphate salt: 5.97, 7.18 (2H), 7.70, 8.05 |
| B | 5.97, 7.15, 7.23, 7.69, 7.95; |
|   | phosphate salt: 5.94, 7.17 (2H), 7.68, 8.05 |
| D | 5.94, 7.09, 7.16, 7.66, 7.90; |
|   | phosphate salt: 5.99, 7.18 (2H), 7.69, 8.05 |
| E | 6.08, 7.15, 7.22, 7.73, 7.92 |
| F | 6.05, 7.16, 7.21, 7.71, 7.96; |
|   | phosphate salt: 5.98, 7.18 (2H), 7.70, 8.05 |
| G | 6.04, 7.16, 7.21, 7.69, 7.99 |
| H | 5.91 (0.5H), 5.93 (0.5H), 7.10 (2H), 7.63, 7.99; |
| (mixture of | phosphate salt: 5.90 (0.5H), 5.93 (0.5H), 7.12 (2H), |
| diastereomers) | 7.63, 8.05 |
| I | 6.03, 7.15, 7.21, 7.73, 7.94 |
| J | 6.07, 7.15, 7.22, 7.73, 7.93 |
| K | 5.75, 6.99, 7.08, 7.67, 7.86 |
| L | 5.89, 7.09, 7.15, 7.67, 7.91 |
| M | 5.90, 7.09, 7.15, 7.68, 7.91 |
| N | 5.93, 7.16, 7.24, 7.72, 7.96 |

The phosphoric salt of Compound C was prepared as follows: Compound C (50 mg) was dissolved in a solvent mixture of acetonitrile (1 mL) and water (1.0 mL) and to this solution was added an aqueous solution of $H_3PO_4$ (0.1 M, 0.38 mL). The resulting mixture was mixed thoroughly and then lyophilized for 28 h to yield 50 mg of the corresponding phosphoric salt. $^1$H NMR peaks at 5.92, 7.11, 7.63 and 8.01 ppm.

Reference Example 1

The aldehyde, [3'-acetoxy-N-methyl-Bmt][(R)-2'-formyl-methoxy-Sar][3] cyclosporin A (290 mg), was dissolved in methanol (15 mL) and to this solution were added acetic acid (30 µL), pyrrolidine (50 µL), and sodium cyanoborohydride (30 mg). The resulting mixture was stirred at room temperature overnight. The solvent was removed and the residue was purified using silica gel column chromatography to yield 154 mg of [3'-acetoxy-N-methyl-Bmt][1][(R)-2'-(2-pyrrolidin-1-yl)ethoxy-Sar][3] cyclosporin A. $^1$H NMR peaks at 5.95, 7.08, 7.16, 7.60 and 7.90 ppm.

Reference Example 2

To a suspension of Dess-Martin periodinane (300 mg) in dichloromethane (30 mL) was added [3'-acetoxy-N-methyl-Bmt][1][(R)-2'-hydroxymethylmethoxy-Sar][3]cyclosporin A (600 mg) in dichloromethane (15 mL) and the resulting mixture was stirred at room temperature for 1 h. The reaction mixture was diluted with MTBE (100 mL), washed with a 1:1 (volume/volume) mixture of 10% $Na_2S_2O_3$ and saturated $NaHCO_3$ (2×50 mL), saturated brine solution, and dried over anhydrous sodium sulphate. After solvent removal, 580 mg of [3'-acetoxy-N-methyl-Bmt]$^1$[(R)-2'-formylmethoxy-Sar]$^3$cyclosporin A was obtained.

Reference Example 3

Camphor sulfonic acid (1.0 g) was added to a solution of [3'-acetoxy-N-methyl-Bmt]$^1$[2'-acetoxy-Sar]$^3$ cyclosporin A (5.14 g) in a solvent mixture of THF (10 mL) and dry ethylene glycol (100 mL), and the resulting mixture was stirred at 50° C. for 5 hours. The reaction mixture was diluted with saturated $NaHCO_3$ (150 mL), water (200 mL), and extracted with ethyl acetate (3×150 mL). The combined organic extracts were washed with water (150 mL), saturated sodium chloride solution (150 mL), and dried over anhydrous sodium sulphate. After solvent removal, 2.66 g of [3'-acetoxy-N-methyl-Bmt]$^1$[(R)-2'-hydroxymethylmethoxy-Sar]$^3$ cyclosporin A was obtained. $^1$H NMR peaks at 5.90, 7.26, 7.46, 8.03 and 8.55 ppm.

Reference Example 4

Mercury acetate (4.4 g) was added to a solution of [3'-acetoxy-N-methyl-Bmt][(R)-2'-thiophenyl-Sar]$^3$ cyclosporin A (4.4 g) in glacial acetic acid (90 mL) and the resulting mixture was stirred for 3 hours at 50° C. The solvent was then removed and the residue dissolved in ethyl acetate (300 mL), washed with a saturated solution of sodium hydrogen carbonate (150 mL) and then brine (150 mL), and dried over anhydrous sodium sulphate. After removal of the solvent, the crude product was purified using silica gel column chromatography to yield 5.14 g of [3'-acetoxy-N-methyl-Bmt]$^1$[2'-acetoxy-Sar]$^3$ cyclosporin A.

Reference Example 5

N,N-Dimethylaminopyridine (1.23 g), triethylamine (1.39 mL) and acetic anhydride (0.63 mL) were added to a solution of [(R)-2'-thiophenyl-Sar]$^3$ cyclosporin A (4.36 g) in dry dichloromethane (60 mL). The resulting mixture was stirred at room temperature for about 2.5 days. The reaction mixture was then diluted with ethyl acetate, washed with water and brine and concentrated. The crude product was purified by chromatography using a silica gel column, eluting with a mixture of ethyl acetate and hexane to yield [3'-acetoxy-N-methyl-Bmt]$^1$[(R)-2'-thiophenyl-Sar]$^3$ cyclosporin A.

Reference Example 6

A solution of cyclosporin A (8.0 g) in dry t-butyl methyl ether (TBME, 50 mL) was added to a suspension of sodium amide (7.0 g) in liquid ammonia (200 mL) at −33° C. under inert atmosphere. The resulting mixture was stirred at −33° C. for 90 minutes under an inert atmosphere. Phenyl disulfide (25 g) was then added, and the reaction mixture was stirred for an additional 2 hours at −33° C. under an inert atmosphere. The reaction was then quenched with solid ammonium chloride (17.5 g) and the ammonia was evaporated. The reaction mixture was then diluted with TBME (250 ml) and water (250 mL), mixed thoroughly, and the layers separated. The organic layer was washed with brine (250 mL) and then concentrated. The residue was purified by chromatography using a silica gel column eluting first with a mixture of ethyl acetate and heptane, and then with a mixture of methanol and ethyl acetate, to yield 4.36 g of [(R)-2'-thiophenyl-Sar]$^3$ cyclosporin A.

5.1 Example 1

Oral Dosage Forms—Formulation of an Oral Capsule

One or more of the compounds for use in the methods provided herein can be formulated as a capsule. Such a capsule can comprise 10 to 100 mg of the compound and on or more excipients selected from the group consisting of microcrystalline cellulose, pregelatinized starch, lactose, sodium starch glycolate, crospovidone, povidone, hydroxypropylcellulose, magnesium stearate and silicon dioxide. The resulting composition can be encapsulated with one or more standard encapsulation compositions such as gelatin or a plasticizer.

5.2 Example 2

Formulation of an Oral Liquid

One or more of the compounds for use in the methods provided herein can be formulated as a salt in a syrup or elixir. The compound or compounds can be at a total concentration of 5 to 50 mg/mL. The syrup or elixir can further comprise polyethylene glycol, propylene glycol, mixtures of polyethylene glycol, PEG 400, a block copolymer of ethylene oxide and propylene oxide (e.g., poloxamer 407), polysorbate 20, ethanol, a sugar, citric acid and/or flavoring.

5.3 Example 3

Formulation of an Ophthalmic Emulsion

The compounds for use in the methods provided herein can be formulated as ophthalmic emulsion. Such an emulsion can comprise in each mL, 0.05% of the compound provided herein and one or more excipients selected from glycerin; castor oil; polysorbate 80; carbomer 1342; purified water and sodium hydroxide to adjust the pH. The resulting formulation can have an osmolality of 230 to 320 mOsmol/kg and a pH of 6.5-8.0.

5.4 Example 4

Formulation of Ophthalmic Drops

The compounds for use in the methods provided herein can be formulated as ophthalmic drops. Such drops can comprise one or more compounds for use in the methods provided herein and one or more excipients selected from purified water as a lubricant, sterile solution hypotonic—borate buffer, electrolytes found in natural tears, sodium chloride, potassium chloride, sodium chloride, sodium bicarbonate, calcium chloride, magnesium chloride, sodium phoshpate, sodium perborate and phosphonic acid stabilizer.

The compounds for use in the methods provided herein can be formulated as ophthalmic drops. Such drops can comprise one or more compounds for use in the methods provided herein and one or more excipients selected from purified water as a lubricant, sterile solution hypotonic—borate buffer, electrolytes found in natural tears, sodium chloride, potassium chloride, sodium chloride, sodium bicarbonate, calcium chloride, magnesium chloride, sodium phosphate, sodium perborate and phosphonic acid stabilizer.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 20 ml solution. One package may contain one or more unit doses. Especially preservative-free solutions are often formulated in non-resealable containers containing up to about twelve, preferably up to about five units doses, where a typical unit dose is from one to about eight drops, preferably one to about three drops. The volume of one drop is about 20-40 μL.

6. BIOLOGICAL ACTIVITY

Murine Mixed Lymphocyte Response (MLR) assay: This assay monitored T-cell proliferation by measurement of tritiated thymidine incorporation into DNA of T-cells isolated from mouse spleens; T-cell proliferation is directly proportional to tritium incorporation into DNA. Pooled spleen cells were prepared from three mice each of two strains: three C57BL/6 and three BALB/c mice. The C57BL/6 mice were used as the Responders (R) and BALB mice were the Stimulators (S) in the MLR. Complete medium consisted of RPMI 1640 supplemented with 25 mM HEPES, 10% heat-inactivated low background fetal bovine serum, 50 μM 2-mercatoethanol, 2 mM L-glutamine, and antibiotics.

The BALB/c spleen cells were gamma irradiated at 3000 Roentgen in a Bevill irradiator and washed once with medium to use as S cells; the stock of S cells was $1.6 \times 10^6$/mL in complete medium. The R cells were stocked at $8 \times 10^5$/mL in complete medium. Final cell densities were $2 \times 10^5$ R and $4 \times 10^5$ S per test well in a 96-well microtiter plate. Compounds were diluted from a 10 mM stock solution in DMSO into culture medium; compounds were tested at 10 concentrations between 0.001 and 30 μM (three-fold dilutions).

Background control wells contained 150 μL of medium/ 0.3% DMSO and 50 μL of R cells ($2 \times 10^5$/well). All other wells contained 100 μL of medium/0.3% DMSO or compound (also in 0.3% DMSO), 50 μL of R cells ($2 \times 10^S$/well), and 50 μL of S cells ($4 \times 10^5$/well). Plates were incubated at 37° C. in 5% $CO_2$ for 5 days, and subsequently pulsed with 1 μCi/well of 3H-thymidine for 6-18 hours. Cells were harvested, and tritium incorporation was measured using a scintillation counter.

Inhibition of T-Lymphocyte Activation in vitro.

Lymphocyte infiltration is one of the main mechanisms of dry eye and uveitis. Therefore, inhibition of T-cell activation provides a basis for treatment of either disease. Assays with human cells are used to determine if compounds I) inhibit T-cell activation (using cytokine release as a biomarker), and 2) reduce or prevent cytokine-induced pathologies.

Compounds were incubated with stimulated human T-lymphocytes in an in vitro system designed to measure cytokine production; cytokine production is indicative of T-cell activation and consequential cytokine-induced damage in vivo. Human T-lymphocytes were isolated (Yssel et al, *J. Immunol. Meth.*, 74: 219) from sites of inflammation from two human donors, labeled P23 and P26. Cells were treated in triplicate with compounds or vehicle (DMSO) in cell culture medium for 2 hours at 37 deg C. Cells were then stimulated with 5 μL of anti-CD3/anti-CD28 ExpandBeads (DynaBeads, Invitrogen 111.31) and incubated for 24 hours. Compounds were tested at three concentrations: 0.02, 0.2 and 2 μM. Untreated controls were performed for each cytokine marker. The following cytokines were quantitatively determined using specific ELISA kits, according to manufacturer instructions: IL2 (Eli-pair, Diaclone), IL4 (ImmunoTools 313.300.49), tumor necrosis factor alpha (TNFα, ImmunoTools 313.330.1), and Interferon gamma (IFN-γ) Eli-pair, Diaclone).

TABLE 1

Inhibition of cytokine production in human T-lymphocytes and the Murine-mixed Lymphocyte Reaction (MLR).

| | Approximate $IC_{50}$ (μM) for cytokine production* | | | | $IC_{50}$ (μM) |
|---|---|---|---|---|---|
| Cmpd | TNF-α | IL4 | IL2 | IFN-γ | MLR |
| A | 2 | 2 | 0.02 | 2 | 0.2 |
| D | 2 | 2 | 1 | 1 | 0.2 |
| F | 0.2 | 0.2 | 0.02 | 0.2 | 0.5 |

*Average value from results of tests from cultures of two donors.

The compounds listed in Table 1 above inhibited cytokine production from stimulated human lymphocytes and in the Murine MLR; no cytotoxicity was observed at the any concentration tested.

The solubilities of compounds in artificial tear formulations were determined using turbidimetric titration (Schote, et al., 2002. *J Pharm Sciences* 91(3):856). The different tear formulations are buffered and contain various physiological electrolytes including, sodium, potassium, phosphate, and chloride. The formulations differ primarily in the "active" ingredients that provide lubrication and viscosity. Compounds were tested for solubility in various artificial tear formulations containing the main classes of active agents: 0.5% carboxymethylcellulose, 0.95% propylene glycol, 0.5% sodium carboxymethylcellulose, 1% Polyethylene glycol 400, plus 1% Polyvinyl alcohol, and 0.1% Dextran 70 and 0.3% hydroxypropyl methylcellulose. The solubilities of N-substituted analogs were determined to be 100 to 2000 μM in various artificial tears (see example below).

TABLE 2

Solubility of Compound A in Artificial Tear Formulations:

| pH | Minimum Solubility (μM) | Other Ingredients (%) |
|---|---|---|
| 6.8 | 130 | Carboxymethylcellulose sodium (0.5) |
| 7.3 | 117 | Propylene Glycol (0.95), Glycerin (0.3) |
| 6.2 | 151 | Polyethylene glycol 400 (1), Polyvinyl alcohol (1) |
| 7.4 | 141 | Dextran 70 (0.1), Hydroxypropyl methyl-cellulose 2910 (0.3) |
| 6.7** | 350 | Dextran 70 (0.1), Hydroxypropyl methyl-cellulose 2910 (0.3) |

**pH was adjusted with HCl from 7.4 to 6.7

Evaluation of Ocular Irritancy Potential Using the HET-CAM Test

The compounds of the invention were evaluated for their potential to be non-irritant to the eye in an in vitro test that is accepted to be predictive of this property known as the HET-CAM test (Steiling, et al., 1999. *Toxicology in Vitro* 13 (2): 375). In this test, chorio-allantoic membranes (CAM) of fertilized chicken eggs are exposed to a solution of the test substance in sterile water. During an incubation period of approximately 5 minutes, irritancy is assessed by visual inspection of the CAM blood vessel network for haemorrhage, lysis and/or coagulation. The time of onset or appearance of each of these effects is scored numerically, the scores are summed to give a single numerical value, and an average numerical score across several eggs is obtained. Based on comparison to historical control substances and vehicle, a classification of irritation potential is obtained (Luepke, 1985. *Food Chem. Toxicol.* 23: 287). The irritancy potential of compounds of this invention is summarized below:

TABLE 3

Irritancy Potential Using the HET-CAM Test:

| Test substance | Lysis | Haemorhage | Coagulation | Total Score | Classification |
|---|---|---|---|---|---|
| Vehicle* | 3 | 0 | 0 | 3.0 | Slightly irritant |
| A | 3.5 | 0 | 0 | 3.5 | Slightly irritant |
| D | 3 | 0 | 0 | 3.0 | Slightly irritant |
| F | 3 | 0 | 0 | 3.0 | Slightly irritant |
| J | 3 | 0 | 0 | 3.0 | Slightly irritant |

*1% (v/v) DMSO in sterile water.

Evaluation of Ocular Tolerability in Rabbits.

The compounds of the invention were evaluated for tolerability upon instillation in the eyes of rabbits over a three day test period. Rabbits receive five instillations within 20 minutes of fifty microliters of a solution of the test substance in vehicle once on Day 1, twice on Day 2 and four times on Day 3 in the right eyes. Evaluation of ocular irritancy was performed using the Draize scale (Draize et al. *J. Pharmacol. Exp. Ther.* 1944. 82: 377). In this evaluation, Compound A (0.05% (w/w) in an artificial tear formulation) was very well tolerated, eliciting only slight conjuctival redness not considered to be significantly different from a vehicle-only treatment group.

The compounds of the invention exhibit both solubility and anti-inflammatory properties that are beneficial in the topical treatment of dry eye and uveitis LPS Induced Uveitis in the Rabbit.

A study is conducted on 12 rabbits to evaluate the effects of the compound on endotoxin-induced acute uveitis in rabbits, based on the procedure described by Allen J B et al., Exp. Eye Res. 1996 January; 62(1):21-8. To induce acute anterior uveitis, *Salmonella typhimurium* lipopolysaccharide endotoxin (LPS) is intravitreally injected into the right eyes of the rabbits. Topical treatment to both eyes of the compound (right eye) or control (left eye), once every 6 hours, of an optimal dose, for example 0.1% w/v, is given to 6 rabbits immediately following intravitreal injection of 10 ng LPS or vehicle (see table below). The four eye groups include a negative control receiving only vehicle (Group1), a positive-uveitis control without drug treatment (group 2), uveitis eye with drug-treatment (group3), and each eye is treated and followed for 7 days. Eyes are evaluated for clinical irritation scores (microscopic ophthalmic examinations), fluorescein dye test, electroretinography (electrodiagnostic method of retinal toxicity), aqueous humor protein concentration and cell counts, and complete ocular histopathology. After the seven days, a favourable response is finding no clinically-significant difference between groups 1 and 3.

Testing Topical Treatment for Dry Eye using Canine Keratoconjunctivitis sicca (KCS) as a Model.

Typical clinical signs of canine KCS include progressive conjunctivitis, superficial keratitis, mucoid ocular discharge, blepharospasm, and ultimately corneal scarring and pigmentary keratitis that results in loss of vision. The disease is bilateral and nearly symmetrical. Diagnosis of KCS is made based on the presence of typical clinical features and a Schirmer tear test (STT) value of less that 10 mm of wetting/minute (Normal is 15-30 mm/min).

Dogs diagnosed with chronic (>3 months in duration) immune-mediated KCS by a veterinary ophthalmologist are selected for treatment. The study is an open label, single group efficacy study using 50 µl (1 drop) of 0.1% compound in each affected eye twice a day. The efficacy of the drug is evaluated based tear production (as measured by the STT), the response of clinical observation of the cornea, and the dog owners' and participating ophthalmologists' overall assessment of efficacy. Physical and ophthalmic examinations (biomicroscopy, indirect ophthalmoscopy) are performed every 2 weeks for the duration of the trial (12 weeks). These examinations include performing STT and assessing severity of the ocular inflammation. The amount of corneal inflammation is subjectively scored for each dog during each examination via biomicroscopy, both before and during the clinical trial. Scores ranging from 0 to 4 (0=normal; 4=most severe) are recorded for 3 parameters: area of corneal vascularization (0, 1-25%, 26-50%, 51-75%, and >75%); severity of loss of transparency (corneal cloudiness—normal, slight, moderate, severe loss of transparency, and opaque), and area of corneal cloudiness (0, 1-25%, 26-50%, 51-75%, and >75%). Results are substantiated by statistical analysis using ANOVA with Tukey-Kramer multiple comparison procedure, a Kruskal-Wallis test, a student's t test, and/or calculation of a Pearson's correlation coefficient (r). All results and probabilities are generated by computerized statistical software (SAS, Inc, Cary, N.C.) and values of P<0.05 are considered significant.

A favorable response to the compound is observed as an increase of 5 mm/min on the STT and substantial improvement in clinical signs (e.g., decreased mucus discharge, blepharospasm, conjunctival hyperemia, etc), as observed by the ophthalmologist within 6 weeks.

All publications and patent applications cited in this specification are herein incorporated by reference as if each individual publication or patent application were specifically and individually indicated to be incorporated by reference. While the invention has been described in terms of various preferred embodiments, the skilled artisan will appreciate that various modifications, substitutions, omissions, and changes may be made without departing from the spirit thereof. Accordingly, it is intended that the scope of the claimed subject matter be limited solely by the scope of the following claims, including equivalents thereof.

What I claim is:

1. A method for treating an ocular disease, wherein the disease is selected from the group consisting of dry eye, uveitis and phacoanaphylactic endophthalmitis, comprising administering to a subject in need thereof a therapeutically effective amount of a compound of general formula (I):

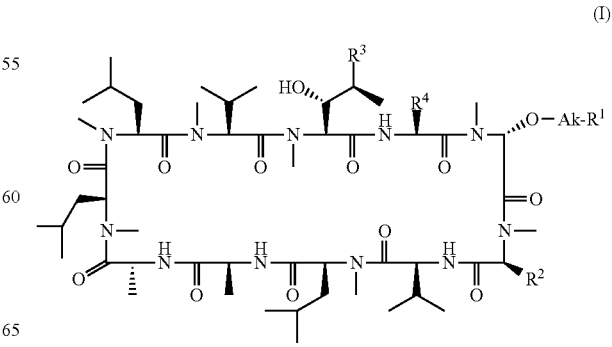

wherein:

Ak is alkylene;

$R^1$ is —$NR^5R^6$, in which $R^5$ and $R^6$ together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four groups which may be the same or different selected from alkyl, hydroxyl, amino, N-alkylamino and N,N-dialkylamino;

$R^2$ is isobutyl;

$R^3$ is (E)-2-butenyl-1 or n-butyl;

$R^4$ is ethyl, 1-hydroxyethyl, isopropyl or n-propyl;

or a pharmaceutically acceptable salt thereof.

2. The method of claim 1, wherein $R^5$ and $R^6$, together with the nitrogen atom to which they are attached, form a saturated or unsaturated heterocyclic ring containing from five to six ring atoms, which ring may optionally contain another heteroatom selected from the group consisting of nitrogen, oxygen and sulfur and may be optionally substituted by from one to four alkyl groups which may be the same or different.

3. The method of claim 2, wherein $R^1$ is N-morpholine.

4. The method of claim 1, wherein Ak is $(CH_2)_p$ and p is two or three; $R^1$ is —$NR^5R^6$; $R^5$ and $R^6$, together with the nitrogen atom to which they are attached, form a saturated or unsaturated heterocyclic ring containing from four to six ring atoms, which ring may optionally contain another heteroatom selected from the group consisting of nitrogen and oxygen and may be optionally substituted by one or two groups which may be the same or different selected from methyl, hydroxyl and dimethylamino; $R^2$ is isobutyl; $R^3$ is (E)-2-butenyl-1; and $R^4$ is ethyl.

5. The method for treating an ocular disease according to claim 1 comprising administering to a subject in need thereof a therapeutically effective amount of (a) a compound of general formula (I) as defined in claim 1, or a pharmaceutically acceptable salt thereof; and (b) a second agent effective for the treatment of the ocular disease.

6. A method for treating dry eye comprising administering to a subject in need thereof a therapeutically effective amount of 3-[2-(morpholin-4-yl)ethoxy]cyclosporin, or a pharmaceutically acceptable salt thereof.

7. A method for treating dry eye comprising administering to a subject in need thereof a therapeutically effective amount of (a) 3-[2-(morpholin-4-yl)ethoxy]cyclosporin, or a pharmaceutically acceptable salt thereof; and (b) a second agent effective for the treatment of dry eye.

* * * * *